United States Patent [19]

Isner et al.

[11] Patent Number: 5,106,386
[45] Date of Patent: * Apr. 21, 1992

[54] CATHETER

[75] Inventors: Jeffrey M. Isner; Richard Clarke, both of Boston, Mass.

[73] Assignee: AngeLase, Inc., Plymouth, Minn.

[*] Notice: The portion of the term of this patent subsequent to Mar. 5, 2008 has been disclaimed.

[21] Appl. No.: 608,290

[22] Filed: Nov. 2, 1990

Related U.S. Application Data

[63] Continuation of Ser. No. 400,702, Aug. 30, 1989, Pat. No. 4,997,431.

[51] Int. Cl.⁵ .............................................. A61B 17/36
[52] U.S. Cl. ...................................................... 606/15
[58] Field of Search ............... 606/7, 14, 15; 128/397, 128/398

[56] References Cited

U.S. PATENT DOCUMENTS 4,785,815 11/1988 Cohen .................................. 606/7 X
4,854,315 8/1989 Stack et al. ...................... 128/398 X

FOREIGN PATENT DOCUMENTS 3718139 12/1988 Fed. Rep. of Germany ........ 606/15

OTHER PUBLICATIONS

Isner et al, "Lasers: Their Potential . . . ", Cardiovascular Medicine, May 1985, pp. 23-25, 26-30, 37.
Lee et al, "Effects of Laser Radiation . . . ", Am. H. J., Sep. 1983, pp. 587-590.

*Primary Examiner*—Lee S. Cohen
*Attorney, Agent, or Firm*—Hugh D. Jaeger

[57] ABSTRACT

A technique for percutaneous treatment of idiopathic hypertrophic subaortic stenosis (IHSS) and hypertrophic cardiomyopathy (HCM). IHSS and HCM are diseases of the heart in which the septum of the left ventricle thickens resulting in reduced ventricular performance. Current treatments involve drug therapy or a medical intervention called an interoperative myotomy/myectomy using the Morrow procedure. The present invention uses laser energy delivered via fiber optics placed percutaneously to irradiate the thickened septum to reduce tissue volume of the septum and enhance left ventricular function.

2 Claims, 9 Drawing Sheets

CATHETER

This application is a continuation of application Ser. No. 07/440,702, filed Aug. 20, 1989, now U.S. Pat. No. 4,997,431.

CROSS REFERENCES TO CO-PENDING APPLICATIONS

This application is related to Ser. No. 400,701, filed Aug. 30, 1989, entitled "Catheter" by the same Assignee of this application.

BACKGROUND OF THE INVENTION

1. Field of the Invention

The subject invention generally relates to treatment of hypertrophic cardiomyopathy (HCM) and idiopathic hypertrophic subaortic stenosis (IHSS), and more particularly, relates to percutaneous treatment of HCM and IHSS using laser ablation.

2. Description of the Prior Art

The symptoms of IHSS and HCM have been known for some time in the medical community. With either disease, an enlargement of the tissue of the chamber wall within the heart serves to interfere with normal cardiac function. In addition to the standard treatments for impaired cardiac function, the problem has been addressed surgically. Andrew G. Morrow, M.D., et al. discusses such a surgical approach in "Operative Treatment in Idiopathic Hypertropic Subaortic Stenosis", Circulation Volume XXXVII, Apr. 1968, pages 589-596. Though the clinical results of Morrow et al. appear to be promising they warn that care must be exercised because an effective operation requires that the knife must be "plunged into the septum until it is out of sight, completely.

The problem of performing the cardiomyoplasty is in part resolved by Jeffrey M. Isner, M.D., et al., in "Laser Myoplasty for Hypertrophic Cardiomyopathy", *American Journal of Cardiology*, Volume 53, 1984, pages 1620-1625. Isner et al. teach the accomplishment of the procedure by the technique of photoablation using an argon laser. However, the main difficulty with the techniques of Morrow et al., and Isner et al., is the requirement to perform a thoractomy. The difficulty of performing a thoractomy and the added mortality is well known.

SUMMARY OF THE INVENTION

The present invention overcomes the difficulties in the prior art treatments for HCM and IHSS by use of a new and novel catheter to photoablate that tissue which impairs cardiac function. The most important advantage is the use of a percutaneous procedure not requiring a thoractomy This significantly reduces the cost, time, trauma, and mortality rate of the procedure.

The present invention is a new technique to treat IHSS or HCM using a percutaneous approach obviating the need for the interoperative Morrow procedure. The invention consists of a method to percutaneously deliver a catheter via the femoral artery or vein to the septal wall of the left ventricle. The catheter is fixed to the wall by an automatic fixation device after which the laser fiber optic tube is inserted into the catheter and positioned at the distal end. The fiber optical assembly is secured to a laser and which is activated to irradiate the tissue. After sufficient volume reduction is achieved by repeated use of laser energy, the device is removed.

In a typical percutaneous procedure to treat IHSS according to the proposed invention, a catheter assembly consisting of a fiber optic tube, an automatic fixation device, a delivery catheter and a guiding catheter with associated connectors is inserted into the human body either in a retrograde fashion through the femoral artery or transceptually through the femoral vein. The catheter is affixed to the septal wall in the hypertrophied region by means of a fixation device contained within the catheter. The laser is then energized for a period of time photocoagulating or ablating the irradiated myocardial tissue. The thermal damage caused by photocoagulation creates a local myocardial infarction with subsequent reduction in B tissue volume. This change decreases the thickness of the septal wall reducing the outflow track gradient and restoring more normal left ventricular performance.

In photocoagulation part of the laser energy is absorbed by the tissue directly underneath the fiber optic probe and part is scattered throughout the tissue, eventually being totally absorbed over a much greater area than the diameter of the fiber optic tube. The absorbed energy raises the temperature of the tissue resulting in a controlled injury and reduced volume of the affected tissue.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

The present invention is a technique for the percutaneous treatment of idiopathic hypertrophic subaortic stenosis (IHSS) and hypertrophic cardiomyopathy (HCM). In IHSS the septal wall near the aortic valve thickens reducing the performance of the left ventricle by partially or completely occluding the orifice. In HCM the thickness of the myocardium increases to the extent that the chamber size is reduced, thereby limiting stroke volume.

The common treatment for either disease is to surgically reduce the thickness by removing some of the muscle tissue (i.e., performing a myectomy) or reforming the myocardium to improve the shape of the inside of the chamber and increase its volume (i.e., cardiomyoplasty). The reforming can be done surgically (i.e., myoptomy) or by inducing a controlled infarct. The present invention provides the apparatus and technique for performing these procedures percutaneously using laser energy.

Figure 1:
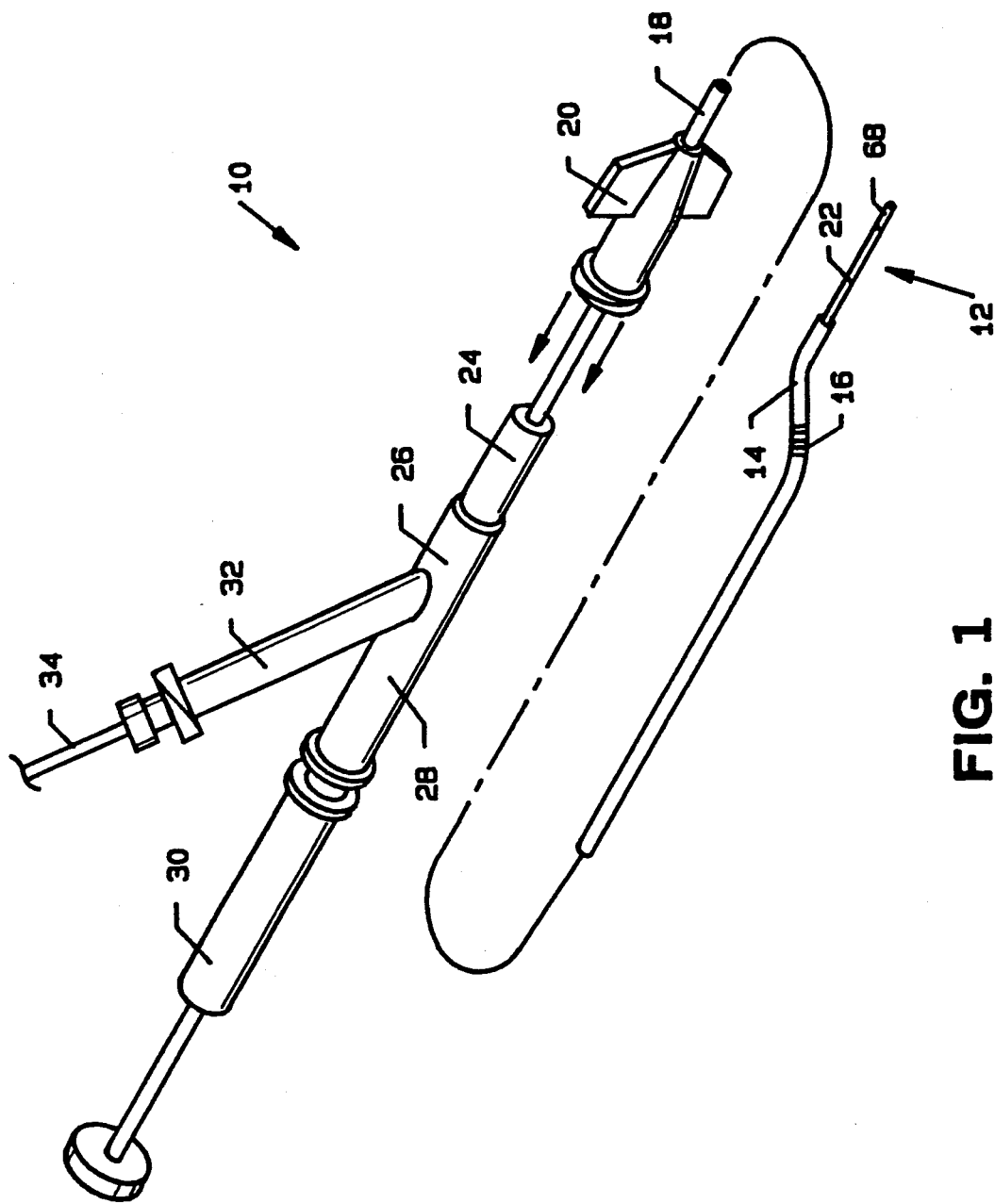
FIG. 1 is a plan view of the catheter of the subject invention.

FIG. 1 is a plan view of catheter 10 of the subject invention. The purpose of catheter 10 is to transmit energy from a medical laser to the myocardium to enable performance of the procedure. This transfer may be transarterial or transveneous as described below. The many aspects of catheter 10 are to optimally facilitate this purpose.

The laser energy is directed to the tissue from distal tip 12. A more detailed view of distal tip 12 is found in FIG. 5. Distal tip 12 is held in position within the ventricle by preformed sigmoidal bend 14 of guiding sheath 10 and fixation wire 42. Distal metal ring 16 provides a radiopaque indication of the location of distal tip 12. For ease of grasping and turning guiding sheath 18, it contains winged member 20 at its proximal end. The distal end of wye 26 frictionally engages the proximal end of guiding sheath 18 during use, but is shown exploded in FIG. 1 to view detail.

Inner catheter 22 runs the entire length of guiding sheath 18. Inner catheter 22 contains the inner lumen through which runs the optical fiber for transmission of the laser energy and the fixation wire 42. Inner catheter 22 is frictionally coupled via swagging or thermoplasty to metal tubing 24 which runs most of the length of wye 26 and defines the inner lumen of main branch 28 of wye 26. Syringe 30 frictionally engages main branch 28 of wye 26.

Secondary branch 32 of wye 26 receives sheath 34 which contains the optical fiber through which the laser energy is transmitted.

Figure 2:
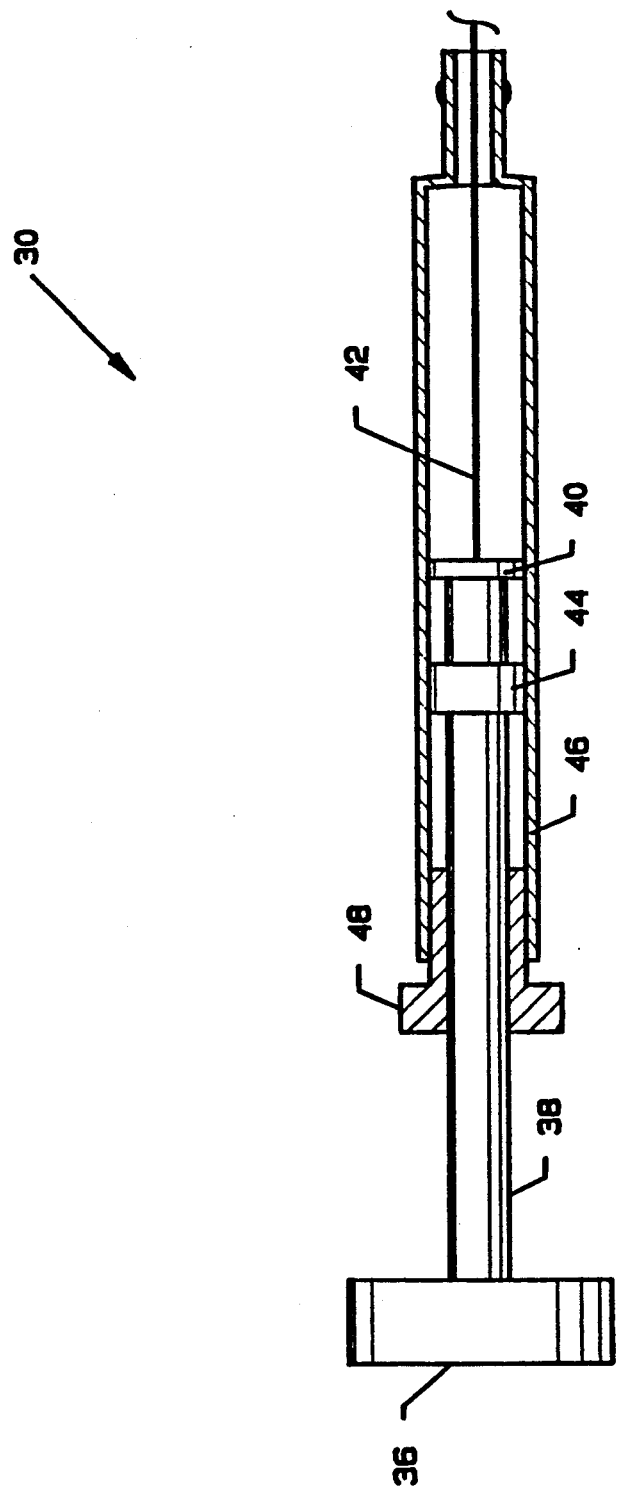
FIG. 2 is a cutaway view of the syringe and the proximal end of the guide wire.

FIG. 2 is a cutaway view of syringe 30. At its most proximal end is thumb knob 36. Depressing thumb knob 36 moves shaft 38 distally which moves piston 40 distally. Fixation wire 42, which runs the entire length of catheter 10, is fixedly attached to piston 40 and is therefore moved distally by pressing thumb knob 36. Fixation wire 42 is substantially stiffer than the inner catheter 22 of catheter 10. The movement of thumb knob 36 (and hence fixation wire 42) in the distal or proximal direction permits medical personnel to maintain the position of distal tip 12 of catheter 10 (see also FIG. 1) and to penetrate the heart tissue for stability (see also FIG. 7).

Rubber seal 44 sealingly engages wall 46 of syringe 30. Configured stopper 48 guides the movement of shaft 38 for smooth operation. Because syringe 30 is airtight, it may be used for resisting inadvertent proximal or distal movement of fixation wire 42.

Figure 3:
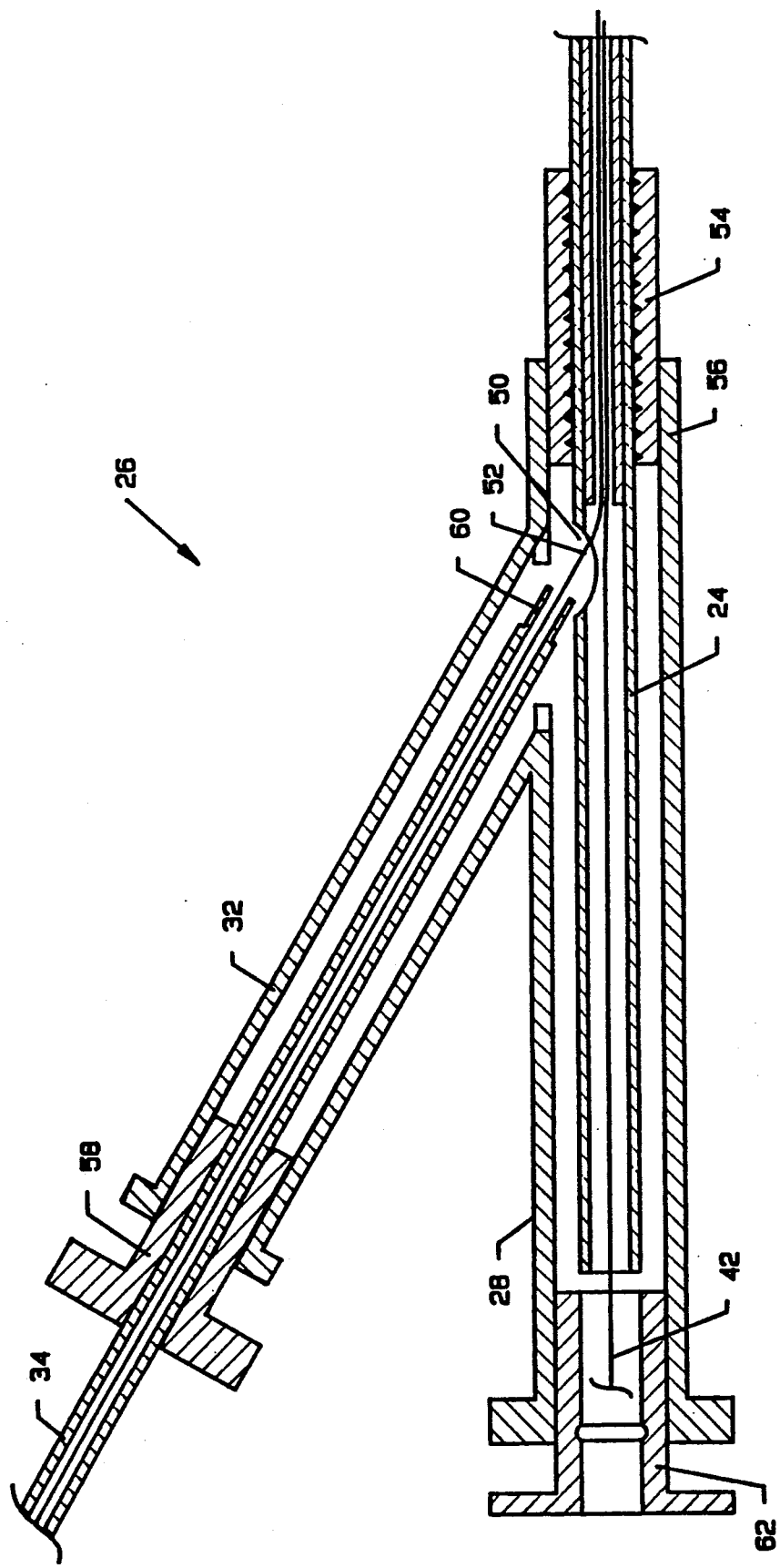
FIG. 3 is a cutaway view of the proximal end of the catheter showing entry of the optical fiber.

FIG. 3 is a cutaway view of wye 26. The outer structure is a molded, rigid plastic. It has a main branch 28 into which syringe 30 is inserted and a secondary branch which receives the optical fiber. As explained above the main branch contains metal tubing 24 which provides a lumen for fixation wire 42. Metal tubing 24 has an aperture 50 which is positioned to receive optical fiber 52. Metal tubing 24 is fixedly engaged by rigid plastic sleeve 54 which in turn is fixedly engaged by the main body of wye 26 and its distal end 56. Rigid plastic sleeve 62 is frictionally engaged by the proximal end of main branch 28. Syringe 30 frictionally engages within the inner diameter of rigid plastic sleeve 62.

Sheath 34 runs the length of secondary branch 32. It provides the lumen for optical fiber 52. Sheath 34 is sealingly engaged by stopper 58 which in turn is sealingly engaged by the proximal end of secondary branch 32. The outer diameter of sheath 34 is decreased at point 60 corresponding to the distal end of secondary branch 32. Sheath 34 terminates at aperture 50 of metal tubing 24.

Figure 4:
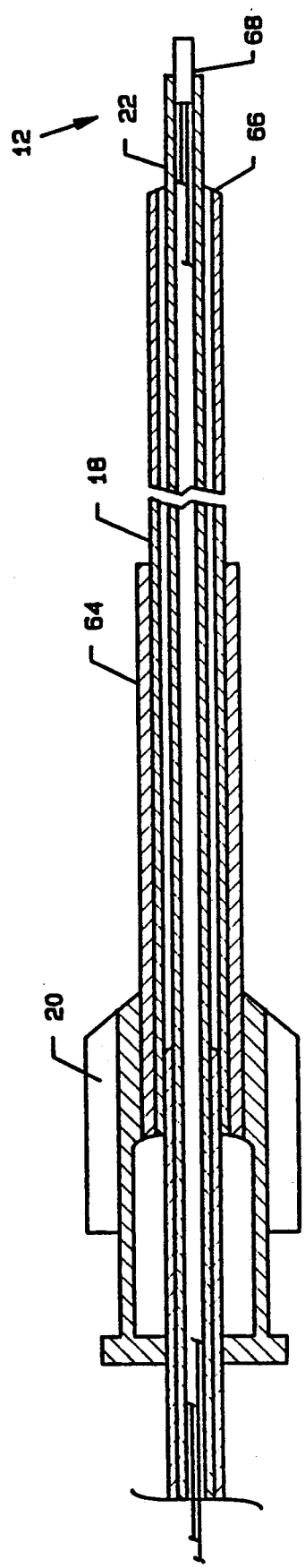
FIG. 4 is a cutaway view of the proximal end of the outer sheath.

FIG. 4 is a cutaway view of the main body of catheter 10. Guiding sheath 18 runs substantially the entire length of catheter 10. Its proximal end is covered by strain relief 64 which is somewhat less flexible than guiding sheath 18, but not rigid. Guiding sheath 18 terminates at point 66 exposing inner catheter 22 which terminates at distal tip 12. Sigmoidal bend 14 and distal metal ring 16 are not shown for clarity, but may be seen in detail in FIG. 5.

Figure 5:
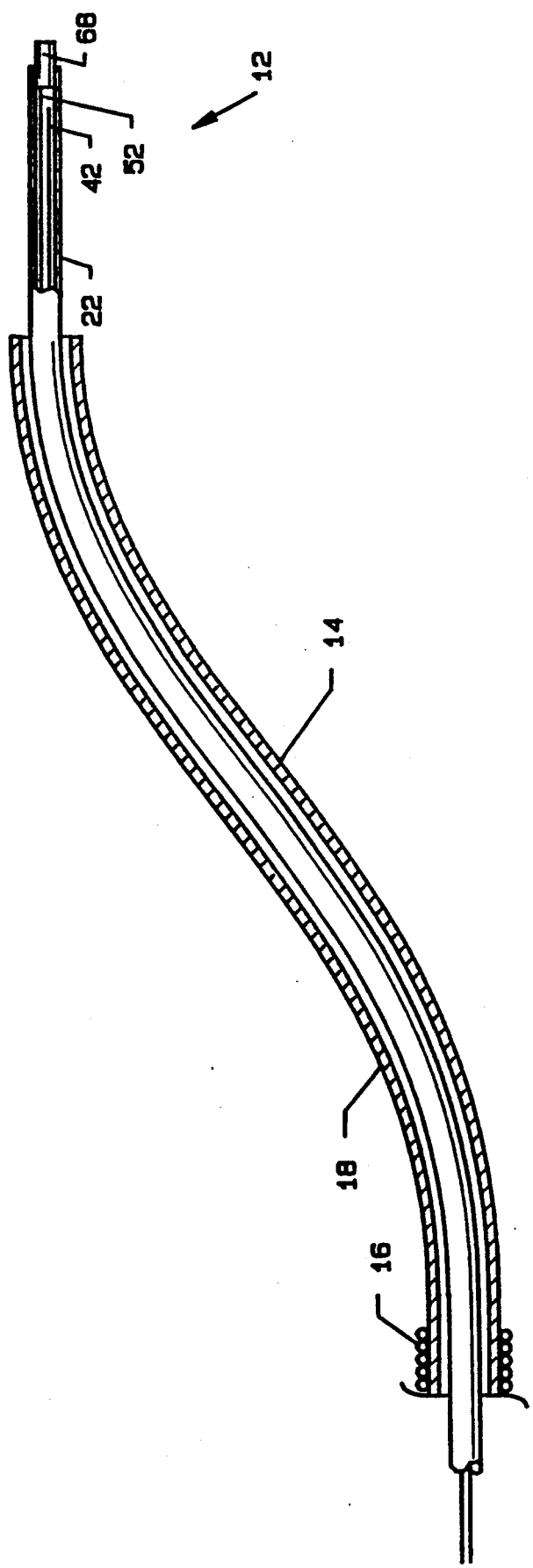
FIG. 5 is a cutaway view of the distal end.

FIG. 5 is a cutaway view of the distal end of catheter 10. Distal tip 12 has a metallic cylinder 68 which frictionally and adhesively engages within inner catheter 22. Metallic cylinder 68 also assists in precisely locating distal tip 12 under fluoroscopy. Optical fiber 52 is fixedly attached within the lumen of metallic cylinder 68 which also aids in energy transfer, in addition to terminating optical fiber 52. Fixation wire 42 terminates just proximal to metallic cylinder 68 when extended maximally in the distal direction. Fixation wire 42 may be advanced and retracted in the manner discussed above to assist in fixation of distal tip 12.

Sigmoidal bend 14 of guiding sheath 18 is preformed. Because guiding sheath 18 is substantially less flexible than inner catheter 22, sigmoidal bend 14 greatly aids in placement of distal tip 12 and in maintaining the desired location. Distal metal ring 16 is placed on sigmoidal bend 14. Because distal metal ring 16 is radioopaque, it is also helpful in identifying sigmoidal bend 14 during the procedure.

Figure 6:
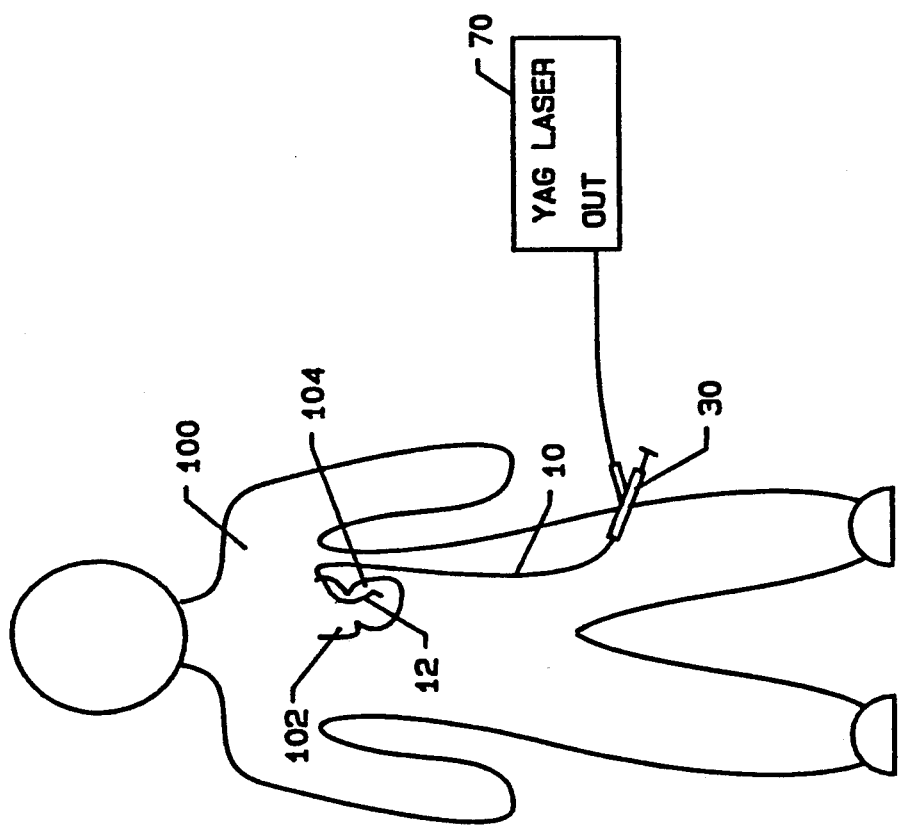
FIG. 6 is a schematic diagram of the procedure using a retrograde femoral approach.

FIG. 6 is a schematic diagram of a percutaneous procedure practicing the present invention. Yag laser 70 is preferably a Model YAG-1 manufactured and sold by Quantronix, Incorporated, although similar products are available elsewhere. Energy from YAG laser 70 is transferred via optical fiber 52 to distal tip 12 placed within left ventricle 104 of heart 102 of patient 100. In this embodiment, catheter 10 is inserted into the femoral artery and proceeds through the aorta into left ventricle 104 via the aortic valve (see also FIG. 7). During operation, the entire catheter system may be cooled by waterflow in the annular space between guiding sheath 18 and inner catheter 22.

Figure 7:
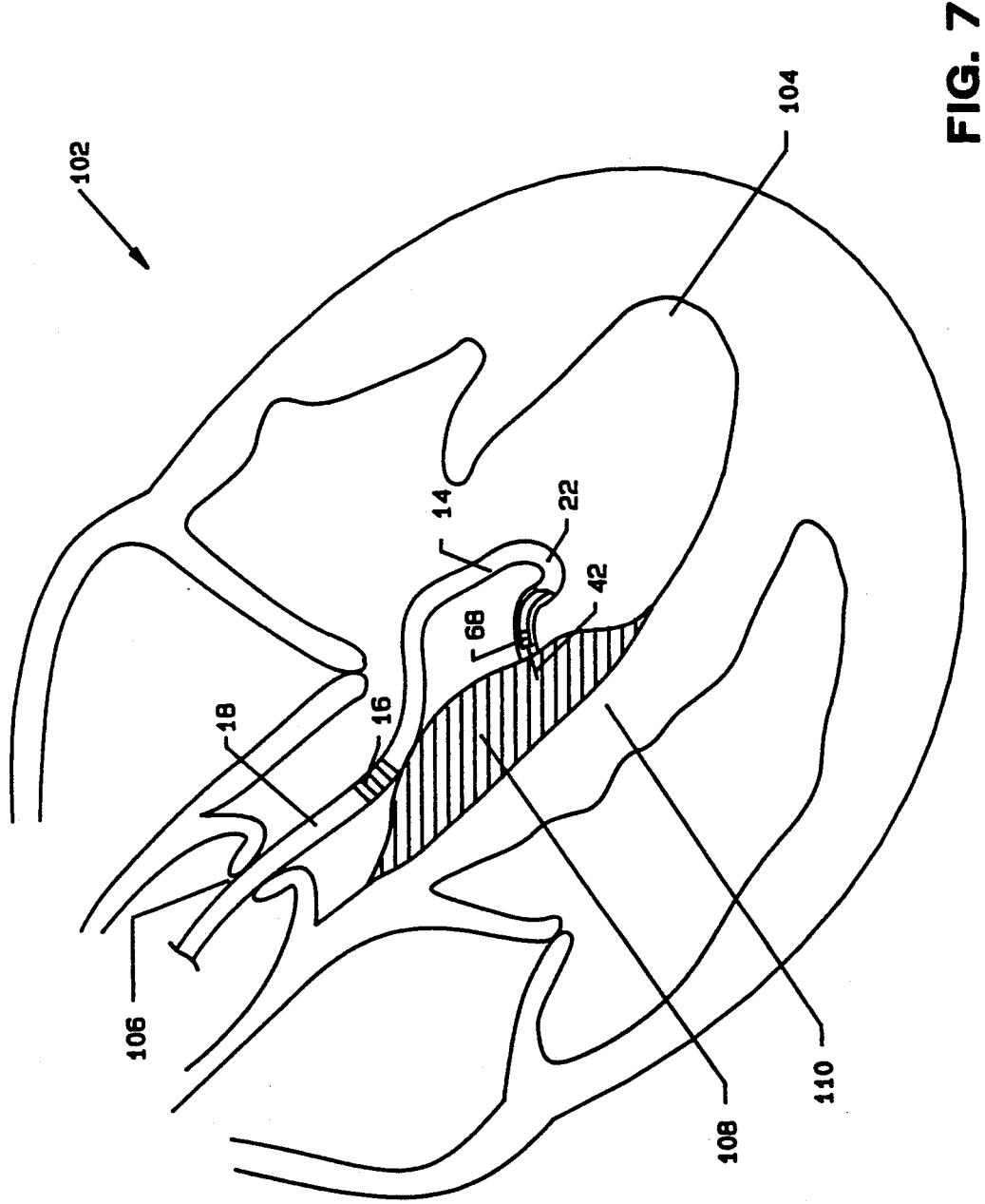
FIG. 7 is a cutaway view of the heart during ablation using a retrograde femoral approach.

FIG. 7 shows an enlarged cutaway view of heart 102 undergoing the procedure of the present invention. As can be seen, left ventricle 104 has had its volume diminished by excessive thickness of septal wall 110 (shaded area) resulting in HCM. Furthermore, the enlargement of septal wall 110 at point 108 interferes with emptying of left ventricle 104 by occluding aortic valve 106 resulting in IHSS.

Catheter IO has been inserted within the femoral artery as shown in FIG. 6 and has been advanced through the aorta into left ventricle 104. Notice sigmoidal bend 14 interacts with the irregular shape within left ventricle 104 to maintain the position of metallic cylinder 68 along the axis of catheter 10. Extension of fixation wire 42 prevents transverse motion. Ideally metallic cylinder 68 is positioned within 1mm of the tissue to be irradiated with the laser energy. Distal metal ring 16 aids in verification of placement using fluoroscopy.

Once the exact position of metallic cylinder 68 is obtained, it is affixed by advancing thumb knob 36 as discussed above.

After Correct placement of metallic cylinder 68 is verified, a short burst of laser energy is issued. Preferably the duration is approximately 15 seconds and the power is approximately 15 watts. This energy is sufficient to either cut the myocardial tissue and thereby reform it or at least produce a controlled infarct which greatly shrinks the tissue volume at the infarct area. In this fashion, the myocardium is reformed to enlarge the chamber volume and alleviate occlusion of the aortic outflow track as described by Morrow.

DESCRIPTION OF THE ALTERNATIVE EMBODIMENT

Figure 8:
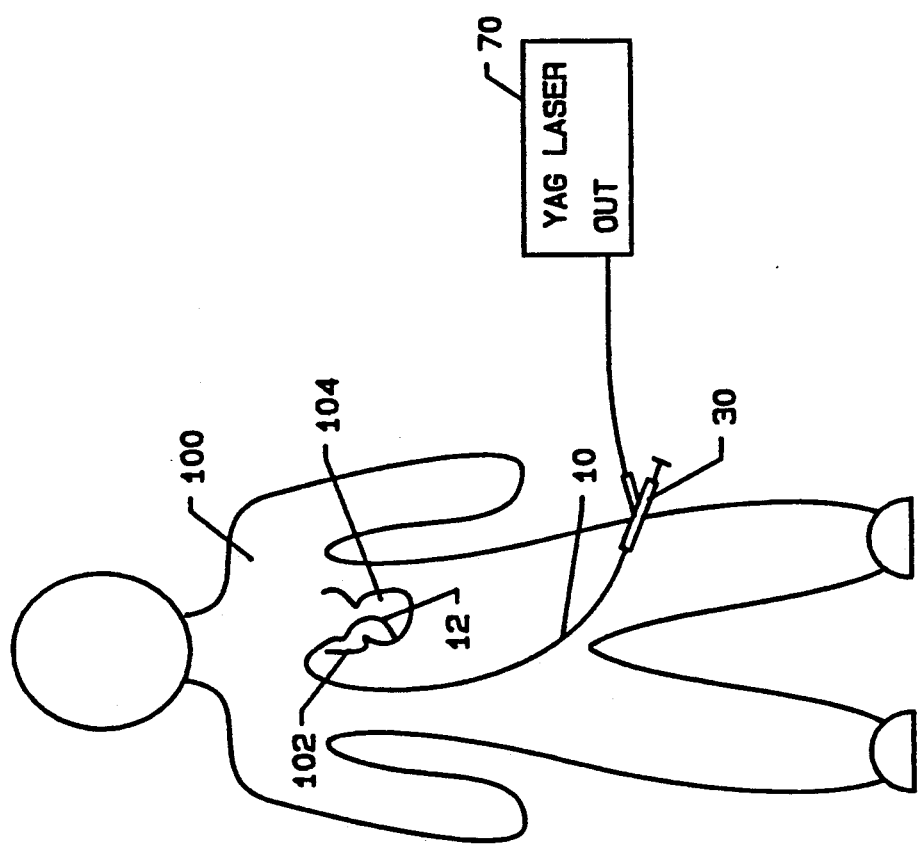
FIG. 8 is a schematic diagram of the procedure using a transceptual approach; and, FIG. 9 is a cutaway view of the heart during ablation using a transceptual approach.

FIG. 8 shows an alternative approach to the procedure. Each of the elements is as shown in FIG. 6. The major exception is that catheter 10 is advanced to heart 102 transveneously. Insertion is preferably made into the femoral vein and is advanced to the right side of heart 102. Left ventrical 104 is entered transeptually as shown in FIG. 9.

Figure 9:
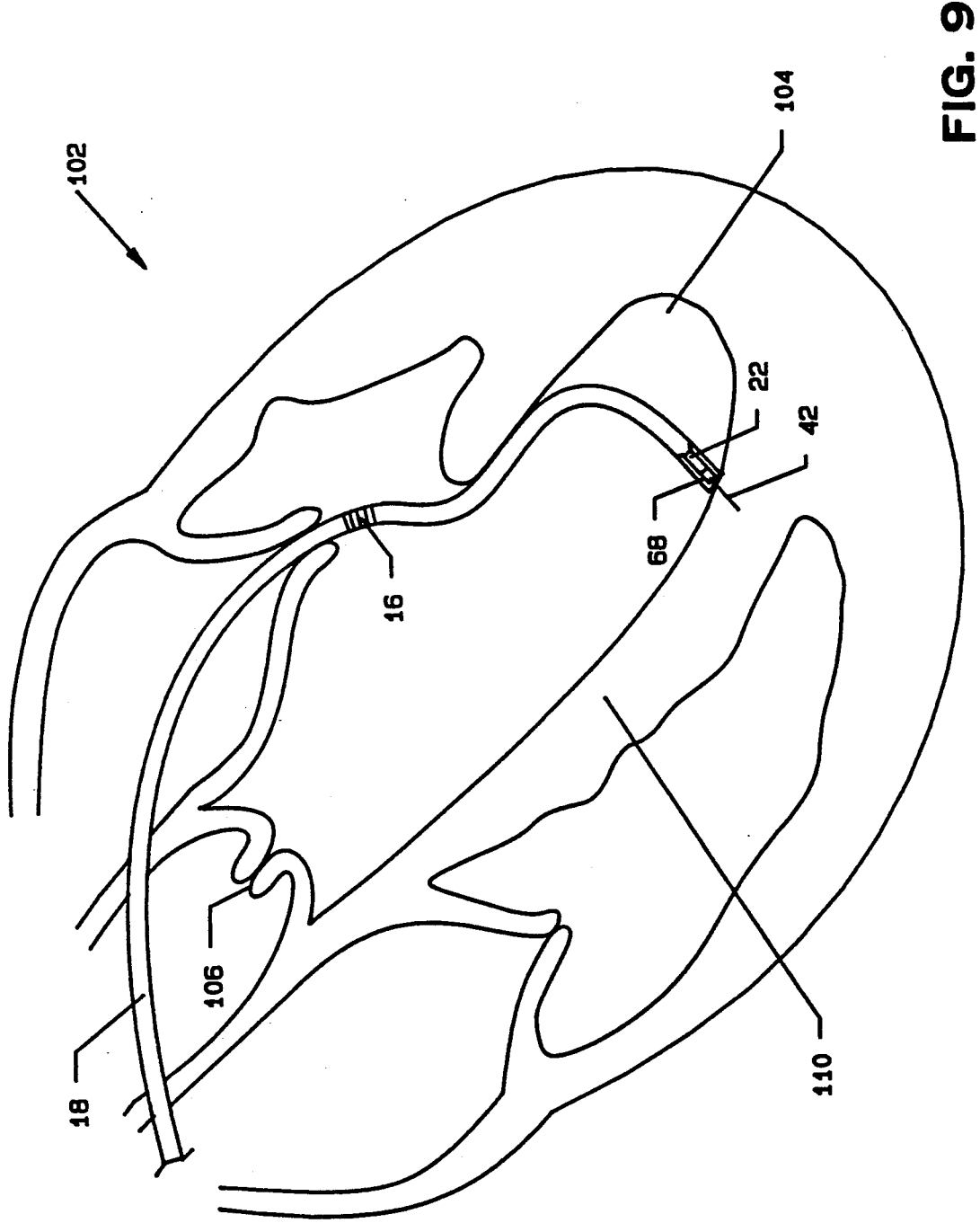

FIG. 9 is a cutaway and enlarged view of heart 102. It differs from FIG. 7 only in that left ventrical 104 is entered transeptually as shown using procedures known in the art.

Having thus described the preferred embodiments of the present invention, those of skill in the art will be able to readily apply these teachings to other embodiments within the scope of the claims hereto appended.

We claim:

1. A process for treating hypertophic cardiomyopathy in idiopathic hypertrophic subaortic stenosis in a patient comprising the steps of:
   a. percutaneously entering a blood vessel of said patient with a distal end of a catheter assembly, said catheter assembly comprising a lumen through which runs an optical fiber and a single fixation wire;
   b. advancing said distal end of said catheter assembly until positioned adjacent myocardial tissue in the heart of said patient;
   c. fixing aid distal end of said catheter assembly adjacent said myocardial tissue by urging a sigmoidal bend of said catheter assembly into contact with the inner walls of said heart and by advancing said fixation wire in said catheter assembly distally so that said fixation wire penetrates tissue of said heart;
   d. advancing a distal end of said optical fiber within said catheter assembly;
   e. coupling a proximal end of said optical fiber to an output of a medical laser; and,
   f. irradiating said myocardial tissue with laser energy transferred from said medical laser to said distal end of said optical fiber.

2. A process according to claim 1 further comprising the steps of:
   a. repositioning said distal end of said catheter assembly until positioned adjacent other myocardial tissue; and,
   b. irradiating said other myocardial tissue with laser energy transferred from said medical laser to said distal end of said optical fiber.

* * * * *

UNITED STATES PATENT AND TRADEMARK OFFICE
CERTIFICATE OF CORRECTION

PATENT NO. : 5,106,386
DATED : April 21, 1992
INVENTOR(S) : Jeffrey M. Isner et al.

It is certified that error appears in the above-indentified patent and that said Letters Patent is hereby corrected as shown below:

Column 2, line 14, "B" should be deleted.

Column 3, line 18, delete "10 and substitute therefor --18--.

Column 6, line 12, delete "aid" and substitute therefor -- said --.

Signed and Sealed this

Twelfth Day of April, 1994

*Attest:*

BRUCE LEHMAN

*Attesting Officer*  *Commissioner of Patents and Trademarks*